US012403332B2

(12) United States Patent
Lee

(10) Patent No.: US 12,403,332 B2
(45) Date of Patent: Sep. 2, 2025

(54) ULTRASOUND OUTPUT DEVICE INCLUDING A PLURALITY OF TRANSDUCERS

(71) Applicant: SKINGRAB CO., LTD., Cheonan-si (KR)

(72) Inventor: Sugun Lee, Paju-si (KR)

(73) Assignee: SKINGRAB CO., LTD., Cheonan-si (KR)

( * ) Notice: Subject to any disclaimer, the term of this patent is extended or adjusted under 35 U.S.C. 154(b) by 316 days.

(21) Appl. No.: 18/104,755

(22) Filed: Feb. 1, 2023

(65) Prior Publication Data

US 2024/0252844 A1 Aug. 1, 2024

(51) Int. Cl.
*A61N 7/00* (2006.01)

(52) U.S. Cl.
CPC ........ *A61N 7/00* (2013.01); *A61N 2007/0034* (2013.01); *A61N 2007/0091* (2013.01)

(58) Field of Classification Search
CPC .............. A61N 7/00; A61N 2007/0034; A61N 2007/0091; A61N 2007/0065; A61N 2007/0073; A61N 2007/0078; A61N 7/02; A61N 2007/0056; A61N 2007/027
See application file for complete search history.

(56) References Cited

U.S. PATENT DOCUMENTS

| 2005/0154313 A1* | 7/2005 | Desilets | A61B 8/4438 600/459 |
| 2011/0077557 A1* | 3/2011 | Wing | A61B 8/546 601/2 |
| 2014/0276055 A1* | 9/2014 | Barthe | A61B 8/4466 600/439 |
| 2017/0050053 A1 | 2/2017 | Barthe et al. | |
| 2019/0105520 A1 | 4/2019 | Sverdlik et al. | |
| 2021/0252314 A1 | 8/2021 | Sverdlik et al. | |
| 2022/0062660 A1 | 3/2022 | Verner Rashkovsky et al. | |

FOREIGN PATENT DOCUMENTS

| JP | 2016-195806 A | 11/2016 |
| JP | 2018-114297 A | 7/2018 |
| KR | 10-1733123 B | 4/2017 |
| KR | 10-2019-0043378 A | 4/2019 |
| KR | 10-2020-0023113 A | 3/2020 |
| KR | 10-2021-0014806 A | 2/2021 |

* cited by examiner

*Primary Examiner* — Bo Joseph Peng
(74) *Attorney, Agent, or Firm* — Invenstone Patent LLC

(57) ABSTRACT

The present disclosure relates to an ultrasound output device having a plurality of transducers, the ultrasound output device comprising: a handpiece in which at least a portion of a lower surface thereof is in contact with or adjacent to a surface of a biological tissue; a transducer module; and a cartridge in which the transducer module is embedded, wherein the transducer module includes a plurality of transducers.

16 Claims, 23 Drawing Sheets

22

ULTRASOUND OUTPUT DEVICE INCLUDING A PLURALITY OF TRANSDUCERS

BACKGROUND

Field

The present disclosure relates to an ultrasound output device including a plurality of transducers.

Description of the Related Art

An ultrasound output device focuses ultrasound on a target region of the skin without causing damage to a skin surface, and induces coagulation necrosis in the target region of the skin. Thereafter, the necrotic target region of the skin can be naturally restored by recovery mechanism for the body's damaged portion.

A conventional ultrasound output device was used by replacing a cartridge suitable for a procedure in a handpiece, and in this case, the cartridge is replaced in a state of being equipped with one transducer.

In each cartridge equipped with a transducer, as a focal distance of the ultrasound of the equipped transducer is differently set, it is necessary to select and replace a suitable cartridge according to a location or depth of the lesion to be operated.

Therefore, there is a continuous demand for development of an ultrasonic output device including a plurality of transducers capable of performing a procedure suitable for a location or depth of each lesion without replacing a cartridge by simultaneously having the plurality of transducers.

SUMMARY

Meanwhile, the inventors of the present disclosure have recognized an inconvenience of having to replace a cartridge suitable for a procedure in a handpiece during the procedure since one transducer is mounted in the cartridge of an ultrasound output device that is generally used for skin care.

Accordingly, the inventors of the present disclosure could recognize a need for an ultrasound output device that outputs appropriate ultrasound according to a lesion location or depth without replacing the cartridge.

Thus, the inventors of the present disclosure have studied and developed an ultrasound output device outputting a plurality of ultrasound waves that are suitable according to lesion locations or depths without replacing a cartridge during a procedure by having a plurality of transducers.

As a result, the inventors of the present disclosure have come to develop an ultrasound output device that simultaneously outputs a plurality of ultrasound waves that are suitable according to lesion locations or depths without replacing a cartridge by including a plurality of transducers.

Accordingly, an aspect of the present disclosure is to provide an ultrasound output device including a plurality of transducers, wherein the plurality of transducers transmit ultrasound to different tissue depths.

Aspects of the present disclosure are not limited to the aspect mentioned above, and other aspects not mentioned will be clearly understood by those skilled in the art from the following description.

According to an exemplary embodiment of the present disclosure, an ultrasound output device including a plurality of transducers is provided.

In this case, the plurality of transducers may transmit ultrasound to different tissue depths and may be configured to have a linear shape. The transducer having a linear shape may be composed of a plurality of pieces, but is not limited thereto.

In addition, according to an exemplary embodiment of the present disclosure, the ultrasound output device including the plurality of transducers may further include a shielding unit on a lower surface of the transducer to reduce edge noise, but is not limited thereto.

In addition, according to an exemplary embodiment of the present disclosure, the ultrasound output device including the plurality of transducers may further include a film on a lower surface of a cartridge to reduce edge noise, but is not limited thereto.

In addition, according to an exemplary embodiment of the present disclosure, the ultrasound output device including the plurality of transducers may include a cooling passage for lowering temperature by injecting cooling gas or cooling water and flowing it to a bottom surface of the cartridge which is detachable in order to prevent skin burns due to heat generated during a procedure. However, it is not limited thereto.

In addition, plurality of transducers can transmit ultrasound toward a target depth of the skin and may have the same or different frequencies to target the same or different lesion locations or depths.

In addition, according to an exemplary embodiment of the present disclosure, the ultrasound output device including the plurality of transducers may further include a movement mechanism, wherein the movement mechanism for transmitting ultrasound to different tissue depths move the transducer module in a vertical direction or a horizontal direction, wherein each of the plurality of transducers transmit ultrasound to the different tissue depths according to the movement mechanism.

In addition, according to an exemplary embodiment of the present disclosure, the ultrasound output device including the plurality of transducers may further include a driving unit allowing for a swing movement and rotate to adjust an ultrasound focus position, but is not limited thereto.

In addition, according to an exemplary embodiment of the present disclosure, the ultrasound output device including the plurality of transducers may further include a source inputting a continuous wave, but is not limited thereto.

In addition, according to an exemplary embodiment of the present disclosure, the ultrasound output device including the plurality of transducers may further include an aperture, wherein a size of focused ultrasound may be adjusted using the aperture.

Details of other embodiments are included in the detailed description and drawings.

According to the present disclosure, by providing an ultrasound output device including a plurality of transducers, it is possible to perform a suitable ultrasound procedure according to a lesion location or depth without replacing a cartridge.

That is, when using the ultrasound output device including a plurality of transducers according to the present disclosure, the plurality of transducers can transmit suitable ultrasound to respective different lesion locations or depths without replacing a cartridge, so that it is possible to perform a more rapid and accurate ultrasound procedure.

The effects according to the present disclosure are not limited by the contents exemplified above, and more various effects are included in the present disclosure.

DETAILED DESCRIPTION OF THE EMBODIMENT

Figure 1A:
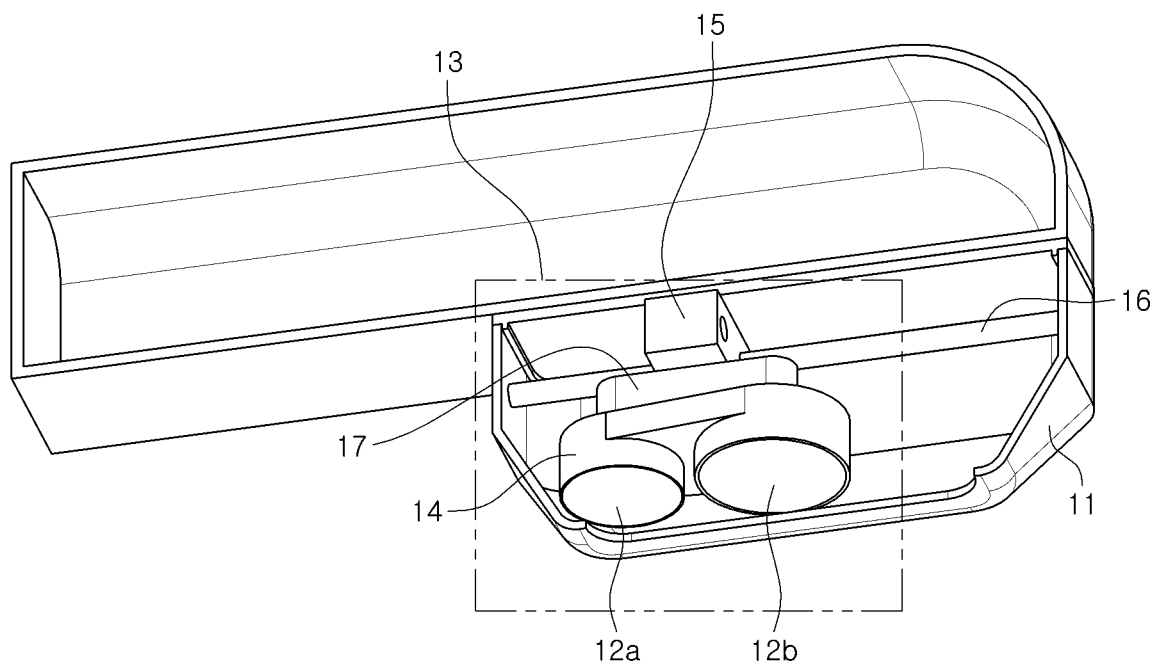
FIG. 1A is a view illustrating an ultrasonic device in which a cartridge housing including a plurality of transducers is disposed in a horizontal direction of a handpiece according to an exemplary embodiment of the present disclosure.

Advantages and features of the present disclosure and methods to achieve them will become apparent from descriptions of embodiments herein below with reference to the accompanying drawings. However, the present disclosure is not limited to the embodiments disclosed herein but may be implemented in various different forms. The embodiments are provided to make the description of the present disclosure thorough and to fully convey the scope of the present disclosure to those skilled in the art. It is to be noted that the scope of the present disclosure is defined only by the claims.

The shapes, sizes, ratios, angles, numbers, and the like illustrated in the accompanying drawings for describing the exemplary embodiments of the present disclosure are merely examples, and the present disclosure is not limited thereto. Like reference numerals generally denote like elements throughout the specification. Further, in the following description of the present disclosure, a detailed explanation of known related technologies may be omitted to avoid unnecessarily obscuring the subject matter of the present disclosure. The terms such as "including," "having," and "consist of" used herein are generally intended to allow other components to be added unless the terms are used with the term "only". Any references to singular may include plural unless expressly stated otherwise.

Components are interpreted to include an ordinary error range even if not expressly stated.

Features of various exemplary embodiments of the present disclosure may be partially or fully combined or coupled. As will be clearly appreciated by those skilled in the art, technically various interactions and operations are possible, and respective embodiments may be implemented independently of each other or may be implemented in association with each other.

Hereinafter, embodiments of the present disclosure will be described in detail with reference to the accompanying drawings.

FIG. 1A is a view illustrating an ultrasonic device in which a cartridge housing including a plurality of transducers is disposed in a horizontal direction of a handpiece according to an exemplary embodiment of the present disclosure.

Figure 1B:
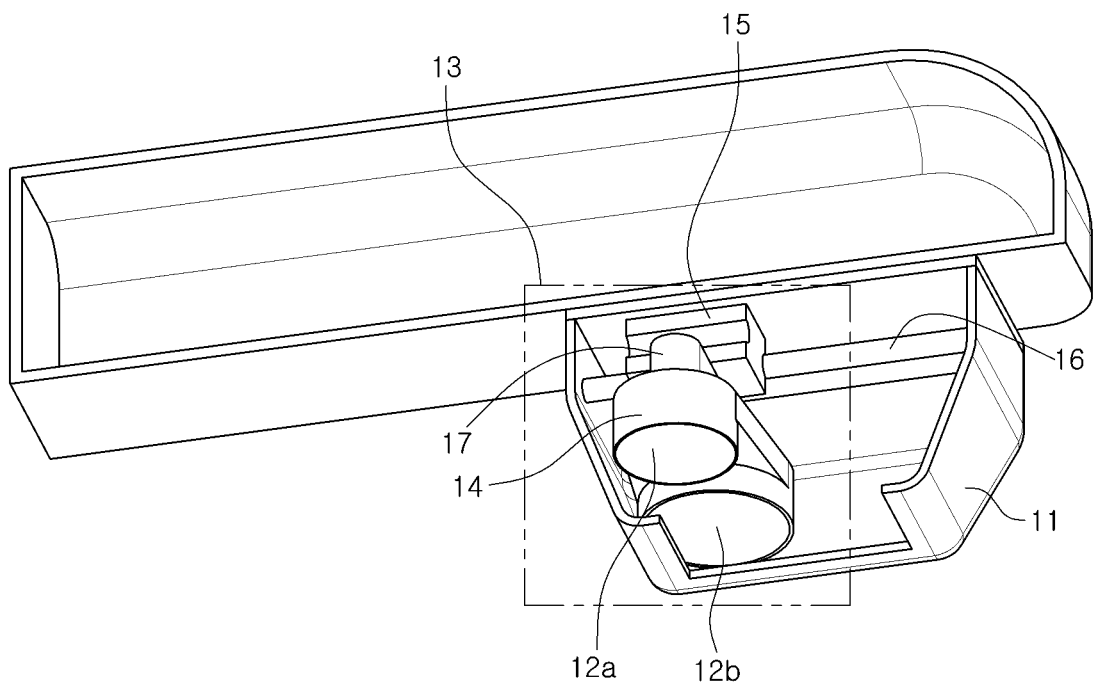
FIG. 1B is a view illustrating the ultrasonic device in which the cartridge housing including the plurality of transducers is disposed in a perpendicular direction of a handpiece according to an exemplary embodiment of the present disclosure.

FIG. 1B is a view illustrating the ultrasonic device in which the cartridge housing including the plurality of transducers is disposed in a perpendicular direction of a handpiece according to an exemplary embodiment of the present disclosure.

Referring to FIGS. 1A and 1B, an ultrasound device including a plurality of transducers according to an exemplary embodiment of the present disclosure includes a handpiece 10, a cartridge 11, a first transducer 12a, a second transducer 12b, a transducer module 13, and a housing 14.

The handpiece 10 is a basic body and may serve as a handle that is gripped by a user.

The cartridge 11 may be detachably coupled to the handpiece 10, and a plurality of the transducers 12a and 12b outputting ultrasound may be provided in the cartridge 11. In this case, the transducers 12a and 12b may receive electrical signals from a power source of the handpiece 10 and focus the ultrasound at a specific location, and the ultrasound may be high-intensity focused ultrasound. In addition, the transducers 12a and 12b can transmit ultrasound toward a target depth of the skin and may have the same or different frequencies to target the same or different lesion locations or depths.

In an exemplary embodiment of the present disclosure, the plurality of transducers 12a and 12b according to the present disclosure may be configured to provide the same frequency, for example, in a range of about 0.1 MHz to 100 MHz. Alternately, the plurality of transducers 12a and 12b according to the present disclosure may be configured to provide different frequencies. In the plurality of transducers 12a and 12b, the first transducer 12a may be selected to provide a central operating frequency in a low range, e.g., from about 0.1 MHz to 10 MHz, and the second transducer 12b may be selected to provide a central operating frequency in a high range from about 10 MHz to 100 MHz.

In another exemplary embodiment of the present disclosure, the first transducer 12a and the second transducer 12b may be set to apply ultrasound therapy with a first ultrasound parameter and a second ultrasound parameter. The first and second ultrasound parameters according to various exemplary embodiments of the present disclosure may be at least one of a variable depth, a variable frequency, and a variable geometrical shape, but the present disclosure is not limited thereto.

In still another exemplary embodiment of the present disclosure, the plurality of transducers 12a and 12b according to the present disclosure performs ultrasound therapy at two or more depths. Each of the two or more interchangeable transducers according to another exemplary embodiment of the present disclosure provides ultrasound therapy at a different depth (e.g., a first transducer targets a 3 mm depth and a second transducer targets a 4.5 mm depth).

The plurality of transducers 12a and 12b according to another exemplary embodiment of the present disclosure performs ultrasound therapy at two or more frequencies, geometrical shapes, amplitudes, velocities, waveforms, and/or wavelengths. The plurality of transducers 12a and 12b according to an exemplary embodiment of the present disclosure may provide at least two or more different depths and two or more different frequencies (or other parameters).

Thus, when using the ultrasound output device of the present disclosure, by including the plurality of transducers 12a and 12b in the ultrasound output device, the same or different lesion locations or depths may be targeted without replacing the cartridge 11.

The transducer module 13 includes the plurality of transducers including the first transducer 12a and the second transducer 12b, a housing 14 having the first transducer 12a and the second transducer 12b, a rail guide 15, a rail unit 16, and a junction unit 17. Thus, the housing 14 having the first transducer 12a and the second transducer 12b is coupled to the rail guide 15 by the junction unit 1 and moves along the rail unit 16 over a target region, while an ultrasound procedure may be performed.

In this case, the ultrasound output device according to the present disclosure may output a continuous wave to allow for an increase in procedure effect.

In an exemplary embodiment, when the ultrasound output device outputs a continuous wave, the plurality of transducers 12a and 12b may be configured to provide the same continuous wave in a range from about 0.1 MHz to 100 MHz. Alternately, the module of the plurality of transducers 12a and 12b according to the present disclosure may be configured to provide different frequencies. In the module of the plurality of transducers 12a and 12b according to the present disclosure, the first transducer 12a may be selected to provide a continuous wave in a low range, for example, from about 0.1 MHz to 10 MHz, and the second transducer 12b may be selected to provide a continuous wave in a high range from about 10 MHz to 100 MHz. However, the present disclosure is not limited thereto.

The transducer module 13 may reciprocally move in a longitudinal direction of the handpiece 10 along the rail unit 16 by the rail guide 15.

In an exemplary embodiment, the plurality of transducers included in the transducer module 13 may be in a direction horizontal to the handpiece 10 (hereinafter, referred to as a horizontal direction of the handpiece 10) as illustrated in FIG. 1A, or may be in a direction perpendicular to the handpiece 10 (hereinafter, referred to as a perpendicular direction of the handpiece 10) as illustrated in FIG. 1B. However, the present disclosure is not limited thereto.

Figure 2A:
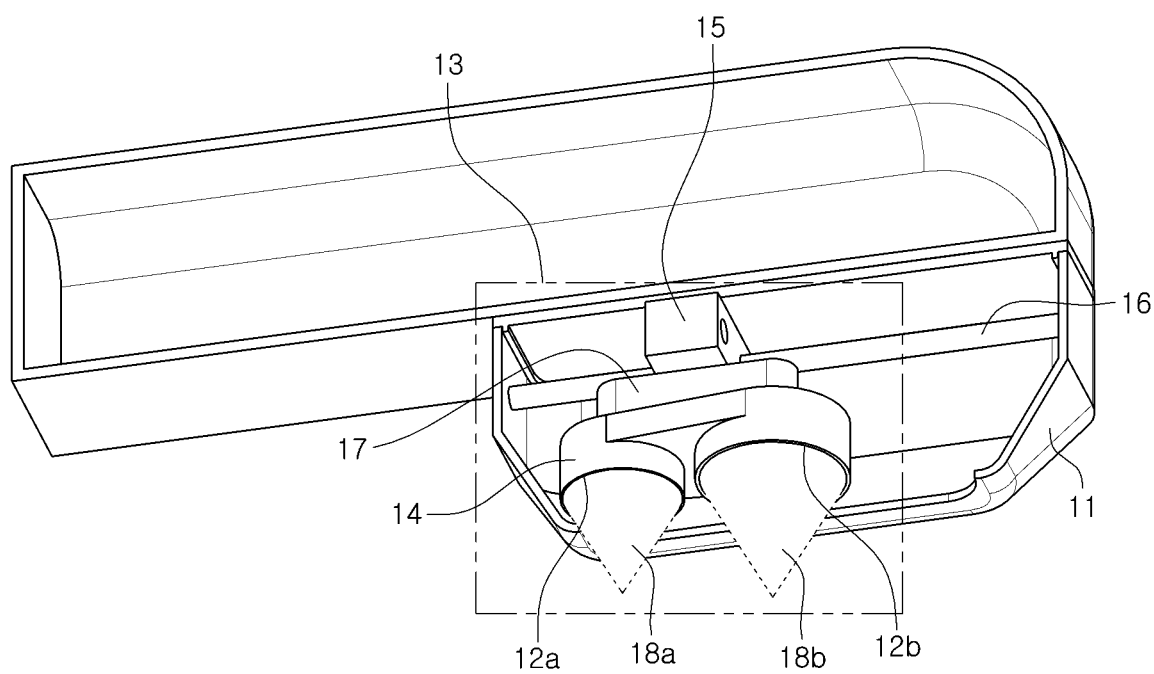
FIG. 2A is a view illustrating a state in which the ultrasonic device where the cartridge housing including the plurality of transducers is disposed in the horizontal direction of the handpiece according to an exemplary embodiment of the present disclosure outputs ultrasound.

FIG. 2A is a view illustrating a state in which the ultrasonic device where the cartridge housing including the plurality of transducers is disposed in the horizontal direction of the handpiece according to an exemplary embodiment of the present disclosure outputs ultrasound.

Figure 2B:
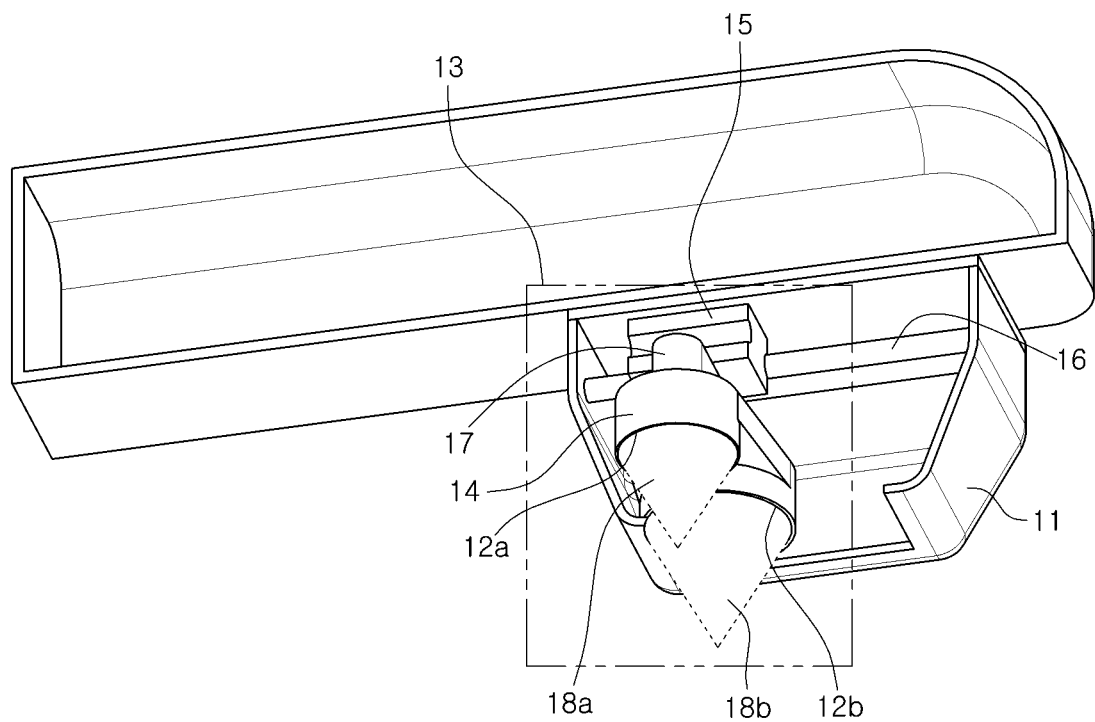
FIG. 2B is a view illustrating a state in which the ultrasound device where the cartridge housing including the plurality of transducers is disposed in the perpendicular direction of the handpiece according to an exemplary embodiment of the present disclosure outputs ultrasound.

FIG. 2B is a view illustrating a state in which the ultrasound device where the cartridge housing including the plurality of transducers is disposed in the perpendicular direction of the handpiece according to an exemplary embodiment of the present disclosure outputs ultrasound.

In an exemplary embodiment, the plurality of transducers included in the transducer module 13 may be coupled to the rail guide 15 in the horizontal direction of the handpiece 10 as illustrated in FIG. 2A or in the perpendicular direction of the handpiece 10 as illustrated in FIG. 2B and reciprocally move along the rail unit 16 in the longitudinal direction of the handpiece 10. However, the present disclosure is not limited thereto.

In an exemplary embodiment, each of the first transducer 12a and the second transducer 12b may have the same or different frequencies to target the same or different lesion locations or depths.

In an exemplary embodiment, when the first transducer 12a and the second transducer 12b have different frequencies to target different lesion locations or depths, the first transducer 12a and the second transducer 12a may output ultrasound of different frequencies, so that focal points 18a and 18b generated by the first transducer 12a and the second transducer 12b may be different from each other.

Figure 3A:
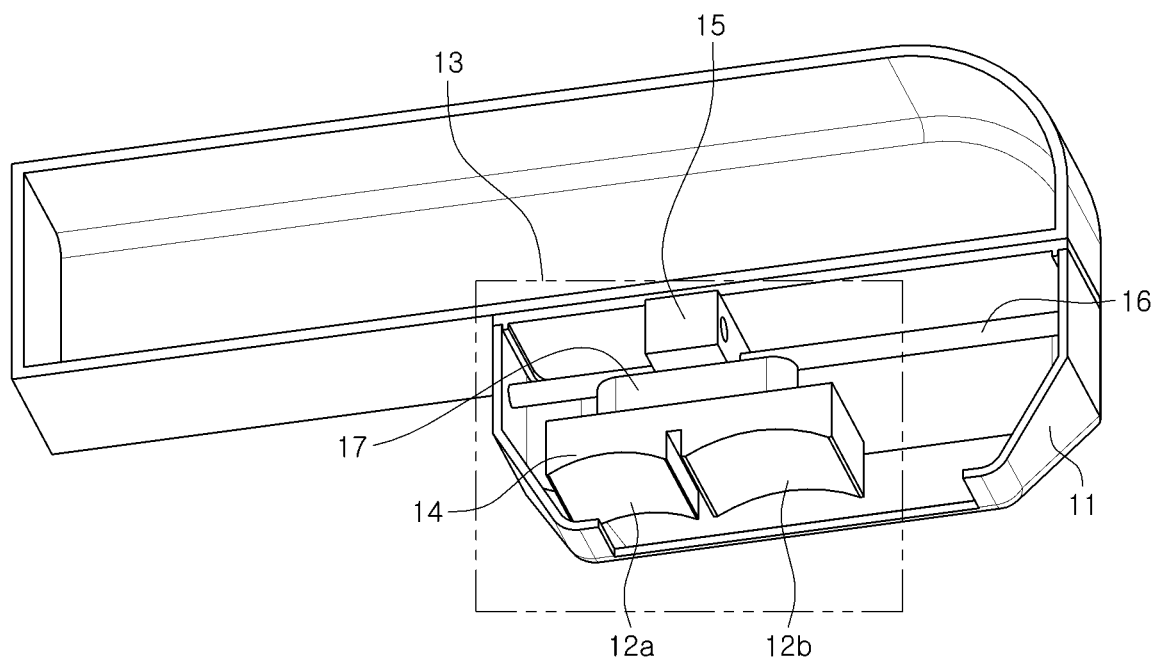
FIG. 3A is a view illustrating an ultrasonic device in which a cartridge housing including a plurality of linear transducers according to an exemplary embodiment of the present disclosure is disposed in a horizontal direction of a handpiece.

In an exemplary embodiment, the plurality of transducers included in the transducer module 13 are coupled to the rail guide 15 in the horizontal direction of the handpiece 10 as illustrated in FIG. 2A or in the perpendicular direction of the handpiece 10 as illustrated in FIG. 2B and reciprocally move along the rail unit 16 in the longitudinal direction of the handpiece 10, while outputting different frequencies. Thus, it is possible to perform an ultrasound procedure on a plurality of target regions in the horizontal direction of the handpiece 10 as illustrated in FIG. 2A or in the perpendicular direction of the handpiece 10 as illustrated in FIG. 2B FIG. 3A is a view illustrating an ultrasonic device in which a cartridge housing including a plurality of linear transducers according to an exemplary embodiment of the present disclosure is disposed in a horizontal direction of a handpiece.

Figure 3B:
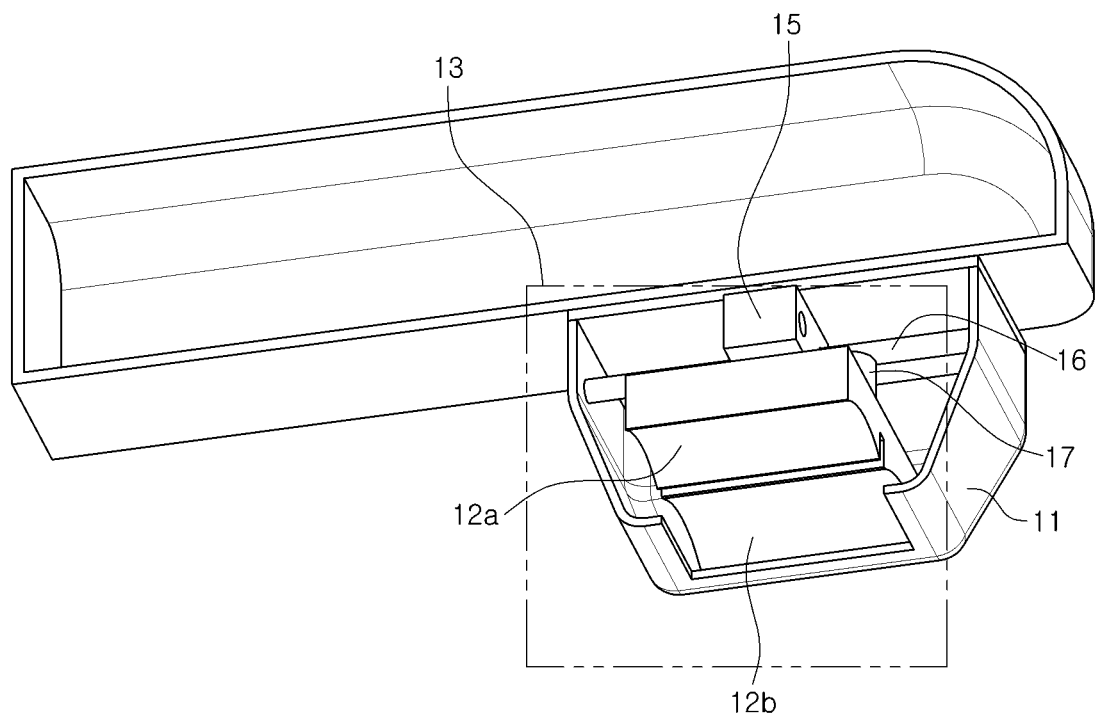
FIG. 3B is a view illustrating the ultrasound device in which the cartridge housing including the plurality of linear transducers according to an exemplary embodiment of the present disclosure is disposed in a perpendicular direction of a handpiece.

FIG. 3B is a view illustrating the ultrasound device in which the cartridge housing including the plurality of linear transducers according to an exemplary embodiment of the present disclosure is disposed in a perpendicular direction of a handpiece.

Figure 3C:
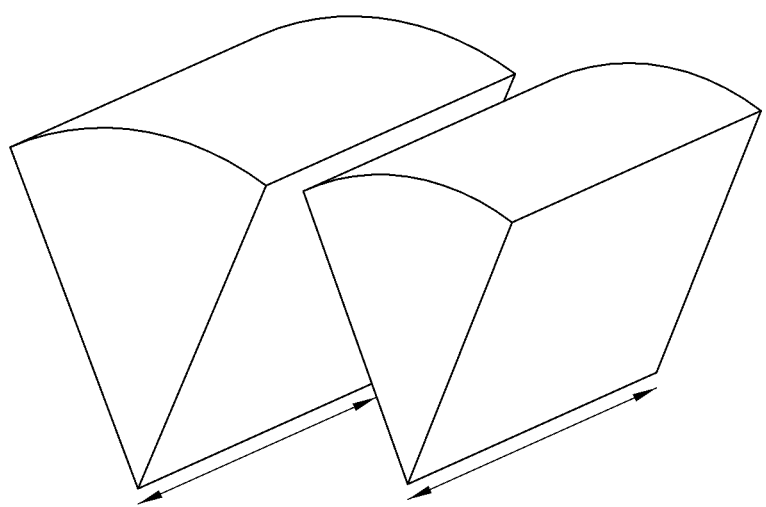
FIG. 3C is a view illustrating focal points when the plurality of transducers have a linear shape according to an exemplary embodiment of the present disclosure.

FIG. 3C is a view illustrating focal points when the plurality of transducers have a linear shape according to an exemplary embodiment of the present disclosure.

In an exemplary embodiment, the first transducer 12a and the second transducer 12b may be linear transducers.

An ultrasonic focal point of a dome-shaped transducer is formed in a form of a point. On the other hand, when the first transducer 12a and the second transducer 12b according to an exemplary embodiment of the present disclosure are linear transducers, since a focal point thereof is formed linearly, an ultrasonic focal point is focused on a wider area than that in dome-shaped transducer. Thus, the effect of an ultrasound procedure is increased and an effect of shortening a procedure time can be expected.

In an exemplary embodiment, in the plurality of transducers included in the transducer module 13, the first transducer 12a and the second transducer 12b are disposed side by side in the horizontal direction of the handpiece 10 as illustrated in FIG. 3A, or the first transducer 12a and the second transducer 12b may be disposed side by side in the perpendicular direction of the handpiece 10, as illustrated in FIG. 3B. However, the present disclosure is not limited thereto.

In an exemplary embodiment, when the plurality of transducers included in the transducer module 13 are disposed in the horizontal direction of the handpiece 10 as illustrated in FIG. 3A, an ultrasound procedure is allowed while the plurality of transducers move by the rail guide 15 and the rail unit 16. However, the present disclosure is not limited thereto.

In an exemplary embodiment, when the plurality of the first transducer 12a and the second transducer 12b included in the transducer module 13 are disposed side by side in the perpendicular direction of the handpiece 10 as illustrated in FIG. 3B, it is possible to perform an ultrasound procedure on a wider area without movement of the plurality of the first and second transducers 12a and 12b. However, the present disclosure is not limited thereto.

Figure 4A:
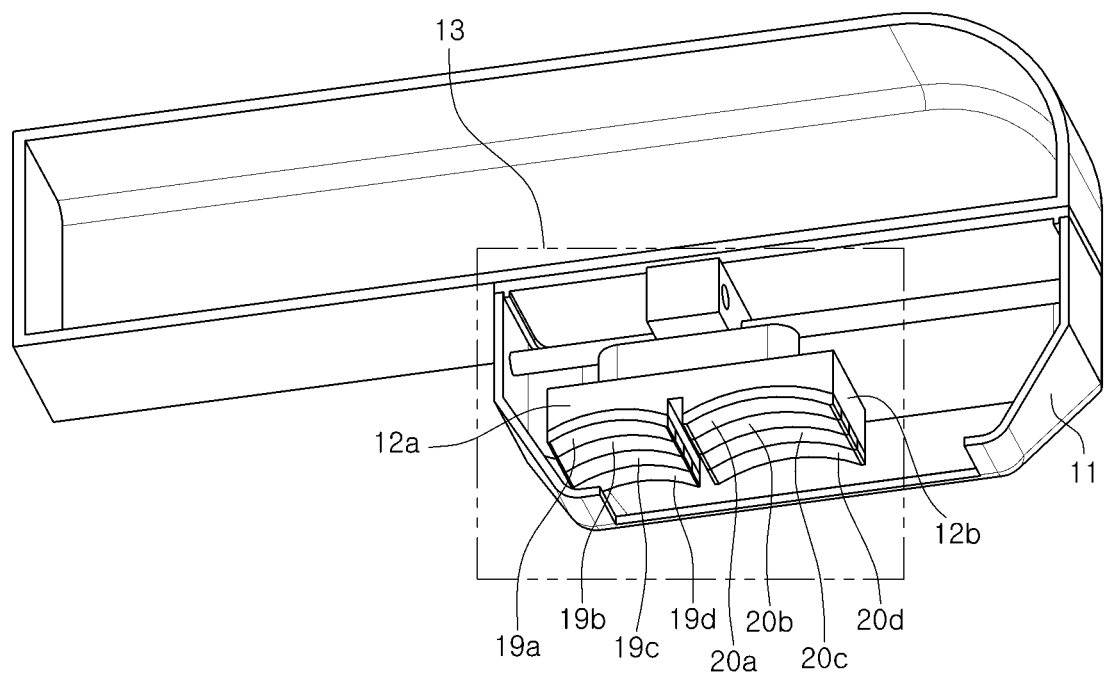
FIG. 4A is a view illustrating an ultrasonic device when a cartridge housing including a plurality of linear transducers is disposed in a horizontal direction of a handpiece and the linear transducers are composed of a plurality of pieces according to an exemplary embodiment of the present disclosure.

FIG. 4A is a view illustrating an ultrasonic device when a cartridge housing including a plurality of linear transducers is disposed in a horizontal direction of a handpiece and the linear transducers are composed of a plurality of pieces according to an exemplary embodiment of the present disclosure.

Figure 4B:
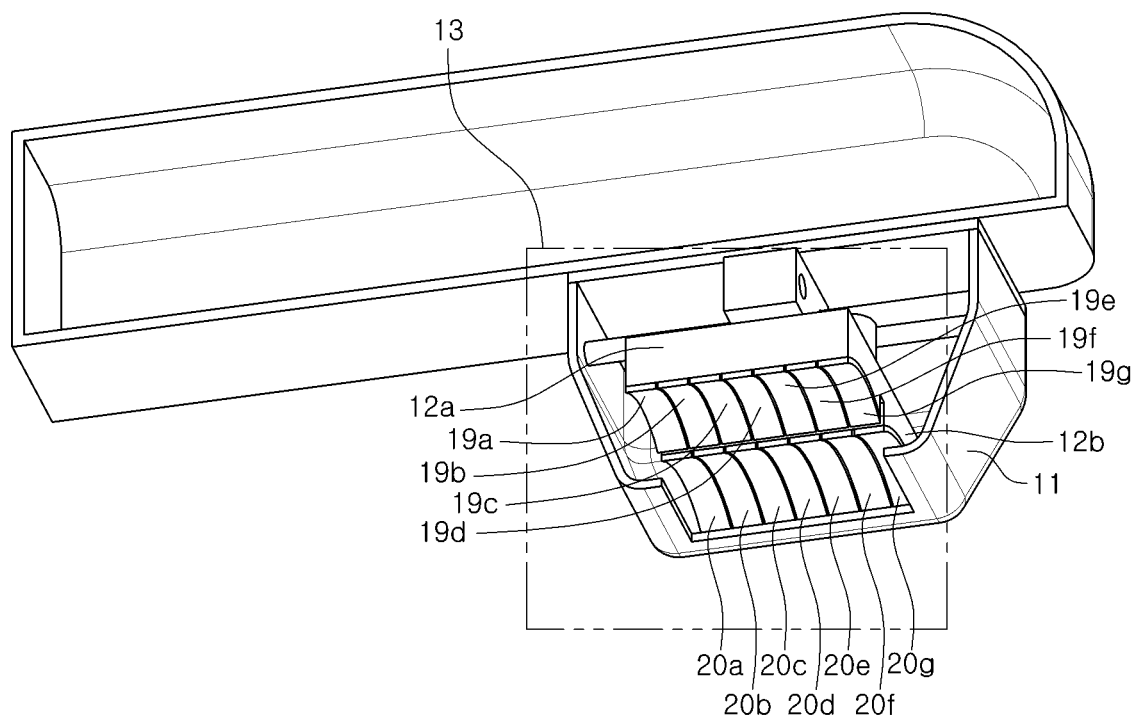
FIG. 4B is a view illustrating the ultrasonic device when the cartridge housing including the plurality of linear transducers is disposed in a perpendicular direction of a handpiece and the linear transducers are composed of a plurality of pieces according to an exemplary embodiment of the present disclosure.

FIG. 4B is a view illustrating the ultrasonic device when the cartridge housing including the plurality of linear transducers is disposed in a perpendicular direction of a handpiece and the linear transducers are composed of a plurality of pieces according to an exemplary embodiment of the present disclosure.

In an exemplary embodiment, the first transducer 12a and the second transducer 12b may be composed of a plurality of pieces 19a to 19d and 20a to 20d.

When the first transducer 12a and the second transducer 12b according to an exemplary embodiment of the present disclosure are linear transducers, the focal point is formed linearly, so that a procedure effect can increase and the effect of shortening a procedure time during an ultrasound procedure can be expected.

In this case, when the first transducer 12a and the second transducer 12b according to an exemplary embodiment of the present disclosure are linear transducers and are composed of a plurality of pieces 19a to 19d and 20a to 20d, a focal point at which ultrasound is focused is formed as plurality of focal points according to the plurality of pieces, Thus, it is possible to reduce edge noise that may occur during an ultrasound procedure.

In an exemplary embodiment, as the plurality of transducers included in the transducer module 13, the first transducer 12a and the second transducer 12b may be disposed side by side in the horizontal direction of the handpiece 10 as illustrated in FIG. 4A, or the first transducer 12a and the second transducer 12b may be disposed side by side in the perpendicular direction of the handpiece 10, as illustrated in FIG. 4B. However, the present disclosure is not limited thereto.

Figure 5A:
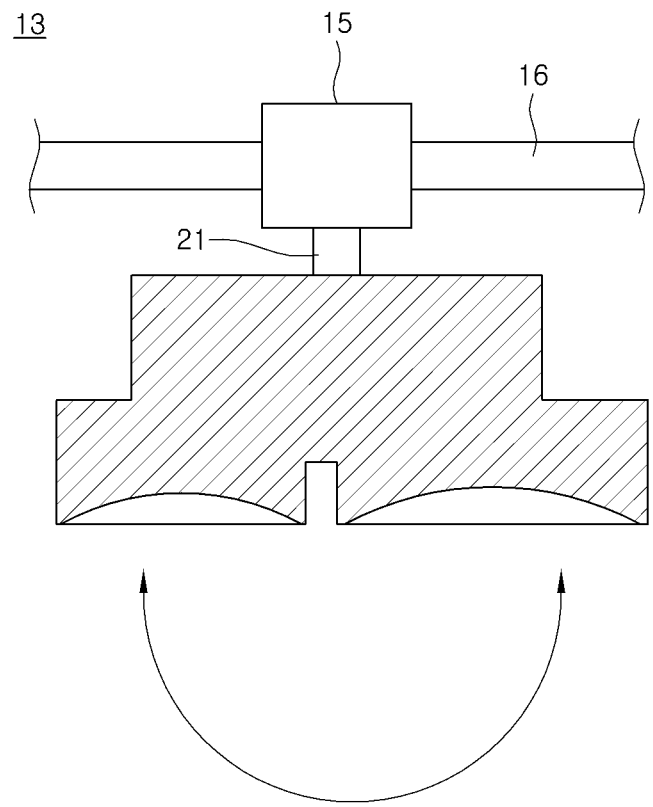
FIG. 5A is a structure view illustrating a state in which the cartridge including the plurality of transducers according to an exemplary embodiment of the present disclosure is rotatably coupled to a hinge unit.

FIG. 5A is a structure view illustrating a state in which the cartridge including the plurality of transducers according to an exemplary embodiment of the present disclosure is rotatably coupled to a hinge unit.

Figure 5B:
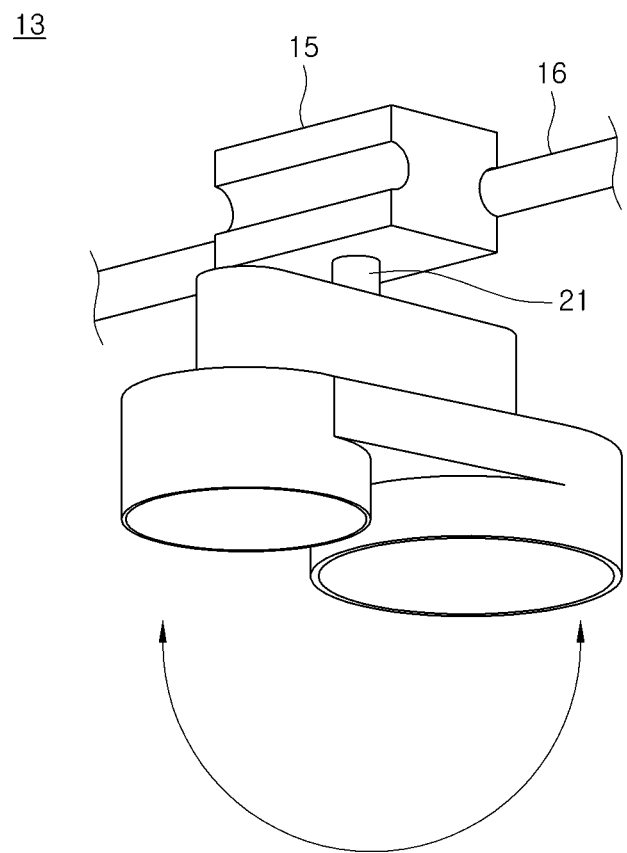
FIG. 5B is a view illustrating a state in which the cartridge including the plurality of transducers according to an exemplary embodiment of the present disclosure is rotatably coupled to the hinge unit.

FIG. 5B is a view illustrating a state in which the cartridge including the plurality of transducers according to an exemplary embodiment of the present disclosure is rotatably coupled to the hinge unit.

Referring to FIGS. 5A and 5B, the ultrasound output device including a plurality of transducers according to the present disclosure may further include a hinge point 21 coupling the rail guide and the housing 14 of the transducers to enable swing movement.

As the swing movement is enabled by the hinge point 21, coupling of the rail guide 15 and the housing 14 may allow for adjustment of an ultrasound focus position and depth.

The hinge point 21 is configured to further include a driving unit capable of a swing movement, so that the swing movement of the housing 14 having the plurality of transducers 12a and 12b is enabled during an ultrasound procedure. Thus, the ultrasound focus position and depth can be adjusted.

Figure 6A:
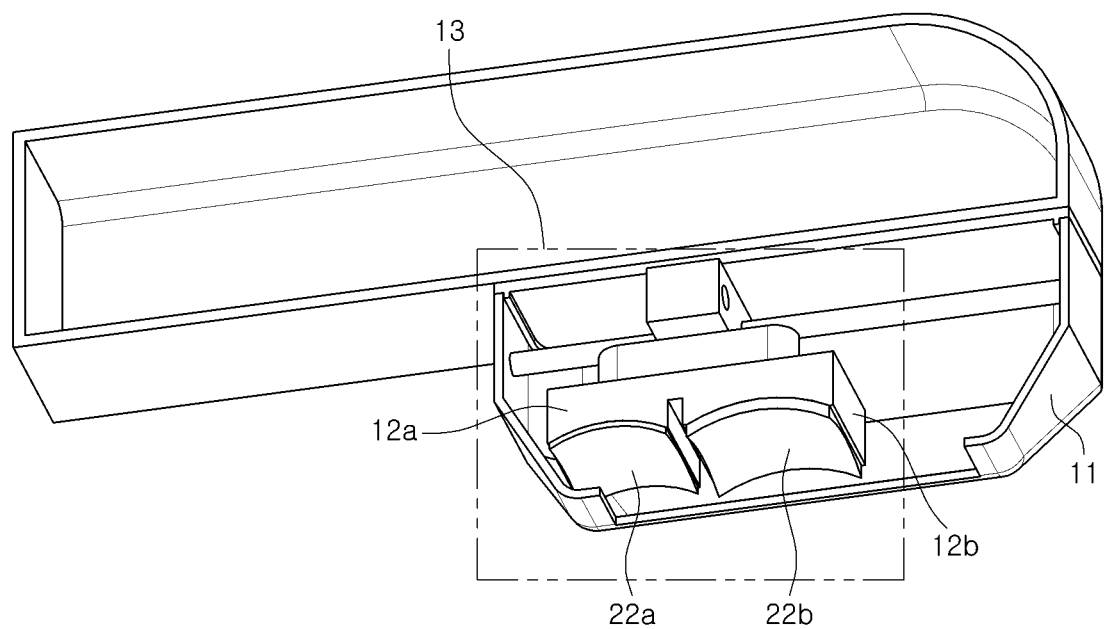
FIG. 6A is a view illustrating a state in which shielding units are coupled to lower surfaces of the plurality of transducers according to an exemplary embodiment of the present disclosure.

FIG. 6A is a view illustrating a state in which shielding units are coupled to lower surfaces of the plurality of transducers according to an exemplary embodiment of the present disclosure.

Figure 6B:
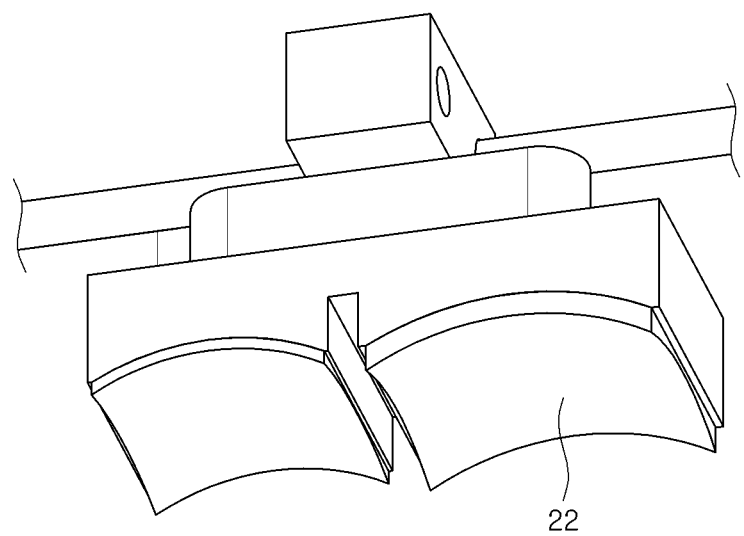
FIG. 6B is a view illustrating shielding units in a state of being coupled to the lower surfaces of the plurality of transducers according to an exemplary embodiment of the present disclosure.

FIG. 6B is a view illustrating shielding units in a state of being coupled to the lower surfaces of the plurality of transducers according to an exemplary embodiment of the present disclosure.

Figure 6C:
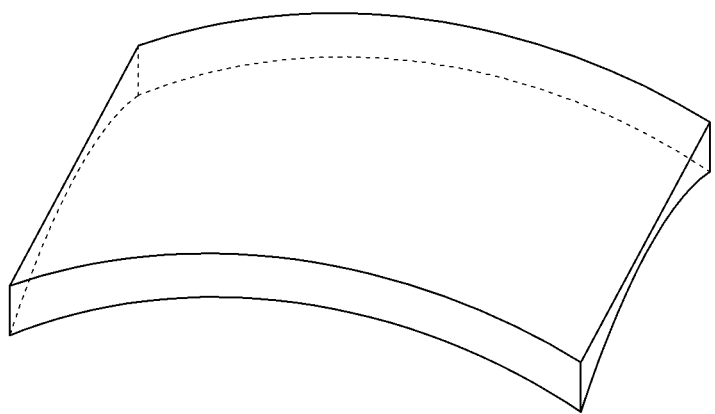
FIG. 6C is a view illustrating the shielding unit coupled to the lower surfaces of the plurality of transducers according to an exemplary embodiment of the present disclosure.

FIG. 6C is a view illustrating the shielding unit coupled to the lower surfaces of the plurality of transducers according to an exemplary embodiment of the present disclosure.

Figure 6D:
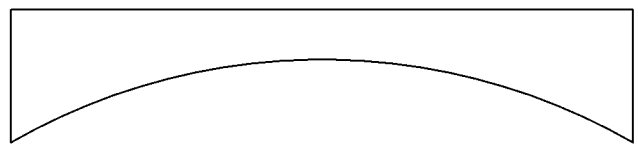
FIG. 6D is a side view of the shielding unit coupled to the lower surfaces of the plurality of transducers according to an exemplary embodiment of the present disclosure.

FIG. 6D is a side view of the shielding unit coupled to the lower surfaces of the plurality of transducers according to an exemplary embodiment of the present disclosure.

Referring to FIGS. 6A to 6B, in an exemplary embodiment of the present disclosure, the first transducer 12a and the second transducer 12b further include shielding units 22a and 22b on their lower surfaces. Referring to FIGS. 6C and 6D, the shielding units 22a and 22b may have a thickness decreasing from a central portion of the transducer to a side portion thereof in order to reduce edge noise that occurs during an ultrasound procedure.

In an exemplary embodiment, the first transducer 12a and the second transducer 12b further include shielding units 22a and 22b on their lower surfaces to thereby reduce edge noise during an ultrasound procedure using the ultrasound output device of the present disclosure. Thus, it is possible to perform the ultrasound procedure with a uniform ultrasound size.

Figure 7A:
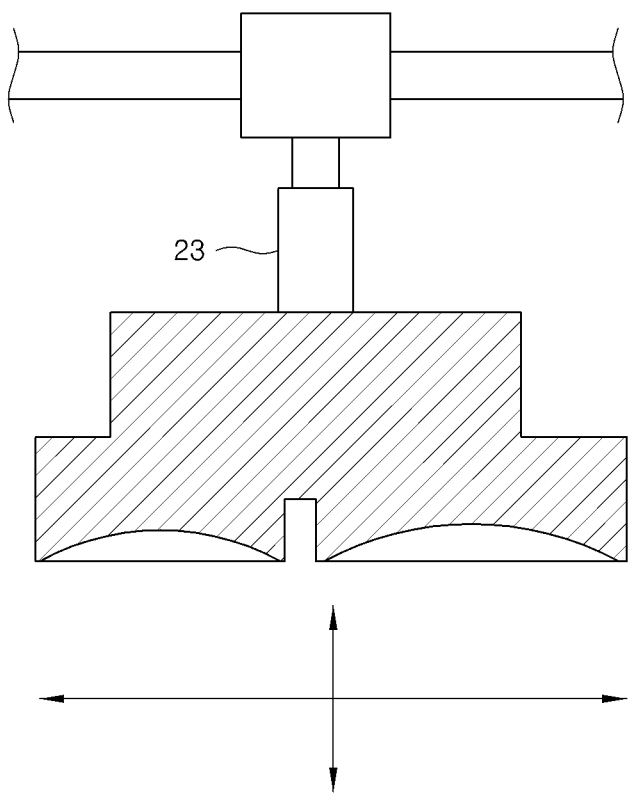
FIG. 7A is a view illustrating a state in which the cartridge including the plurality of transducers according to an exemplary embodiment of the present disclosure is coupled to a driving unit.

FIG. 7A is a view illustrating a state in which the cartridge including the plurality of transducers according to an exemplary embodiment of the present disclosure is coupled to a driving unit.

Figure 7B:
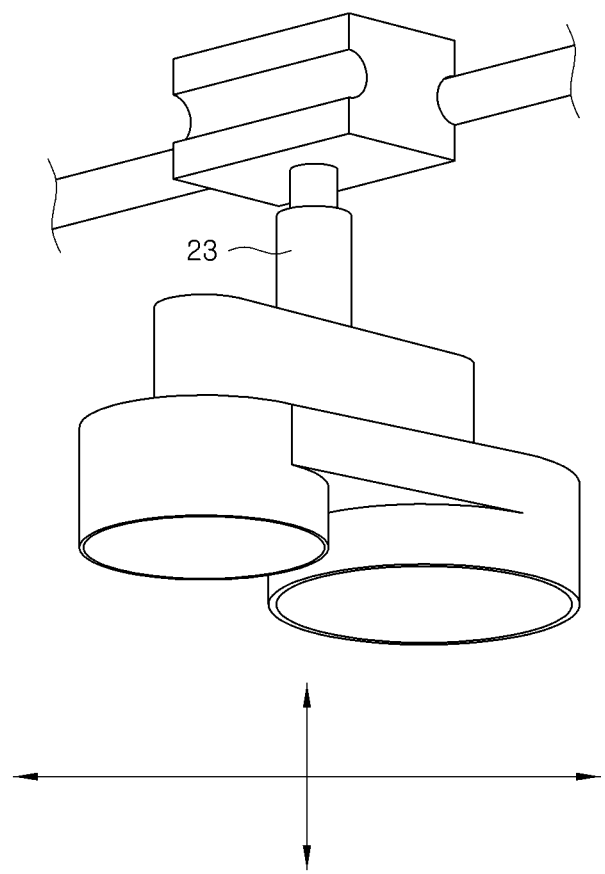
FIG. 7B is a view illustrating a state in which the cartridge including the plurality of transducers according to an exemplary embodiment of the present disclosure is coupled to the driving unit.

FIG. 7B is a view illustrating a state in which the cartridge including the plurality of transducers according to an exemplary embodiment of the present disclosure is coupled to the driving unit.

Referring to FIGS. 7A and 7B, the ultrasound output device including the plurality of transducers according to the present disclosure may further include a driving unit 23.

In this case, the driving unit 23 and the transducer module 13 may include a movement mechanism to deliver ultrasound to different tissue depths. The movement mechanism allows for up and down and left and right movement mechanism and swing movement, so that an ultrasound focus position can be adjusted during a procedure and ultrasound can be delivered to different tissue depths.

In an exemplary embodiment, the driving unit 23 may include a driving motor (not illustrated), and the transducer module 13 may move in a vertical direction and a horizontal direction or may swing by the driving motor during an ultrasound procedure.

Figure 8A:
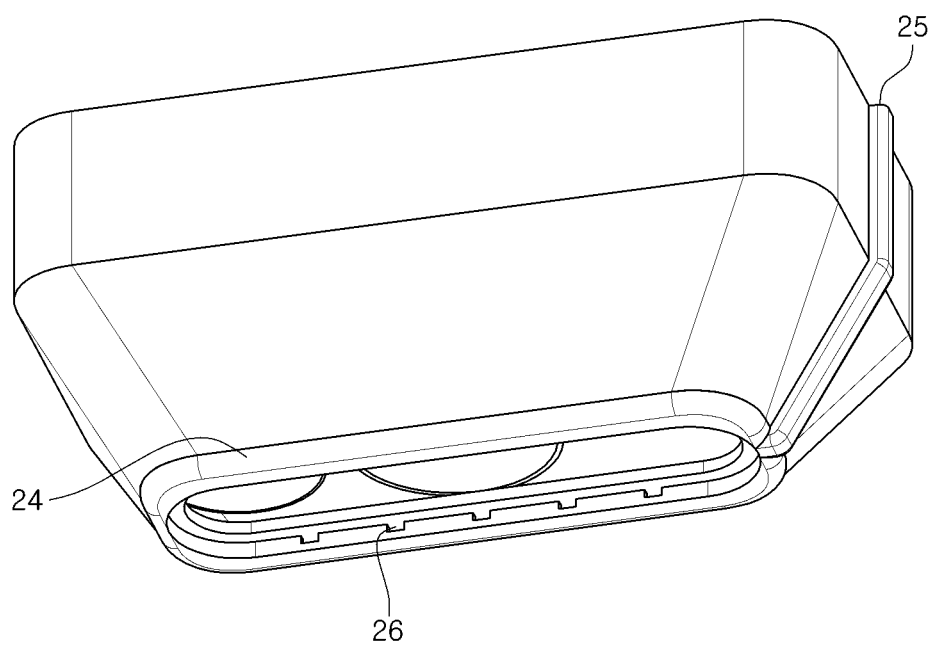
FIG. 8A is a view illustrating a cooling passage coupled to the cartridge including the plurality of transducers according to an exemplary embodiment of the present disclosure.

FIG. 8A is a view illustrating a cooling passage coupled to the cartridge including the plurality of transducers according to an exemplary embodiment of the present disclosure.

Figure 8B:
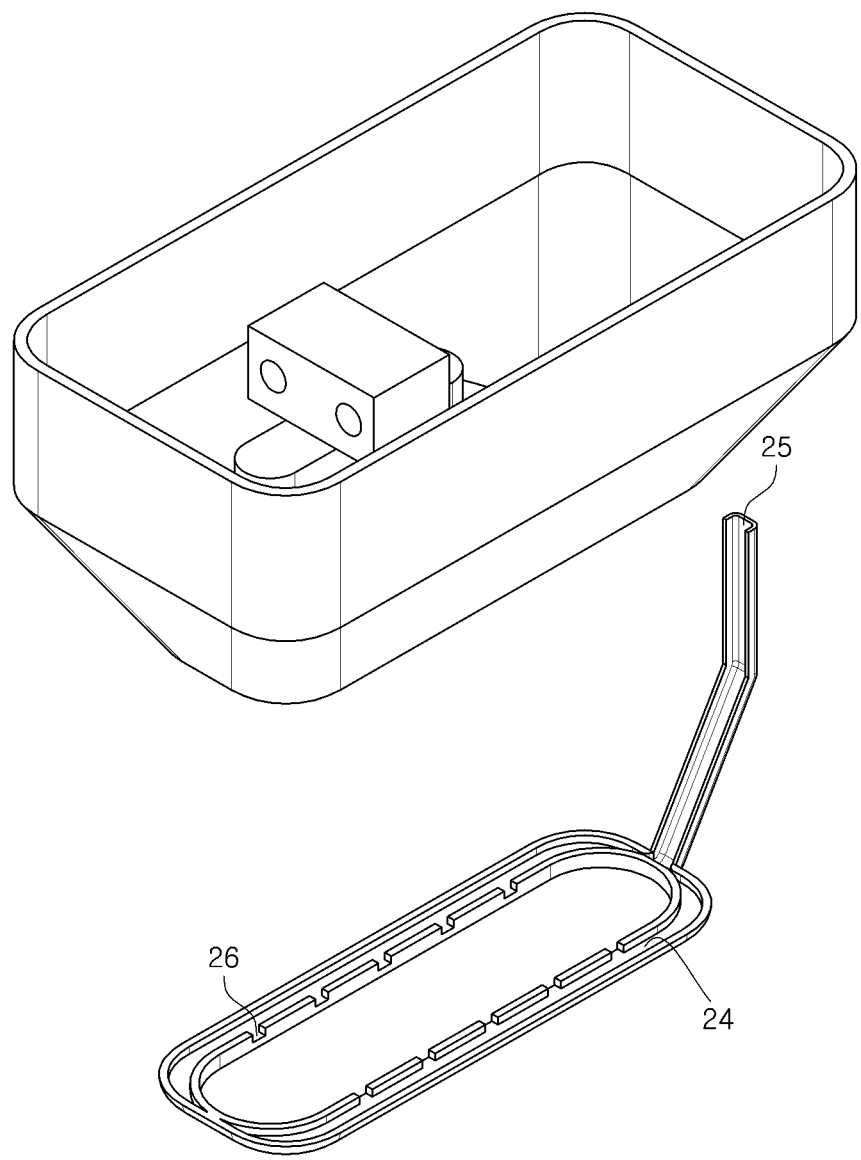
FIG. 8B is a view illustrating the cooling passage coupled to the cartridge including the plurality of transducers according to an exemplary embodiment of the present disclosure.

FIG. 8B is a view illustrating the cooling passage coupled to the cartridge including the plurality of transducers according to an exemplary embodiment of the present disclosure.

Referring to FIGS. 8A and 8B, the ultrasound output device including the plurality of transducers according to the present disclosure may further include a cooling passage 24.

The cooling passage 24 may lower temperature by injecting cooling gas or cooling water into the cartridge 11 through an inlet 25 and flowing the cooling gas or cooling water to a lower surface of the cartridge 11 which is detachable through an outlet 26 during a procedure using the ultrasound output device of the present disclosure.

Therefore, during an ultrasound procedure using the ultrasound output device of the present disclosure, the temperature of the lower surface in contact with or adjacent to a surface of a biological tissue can be lowered using cooling gas or cooling water, thereby preventing the risk of burns.

Figure 9A:
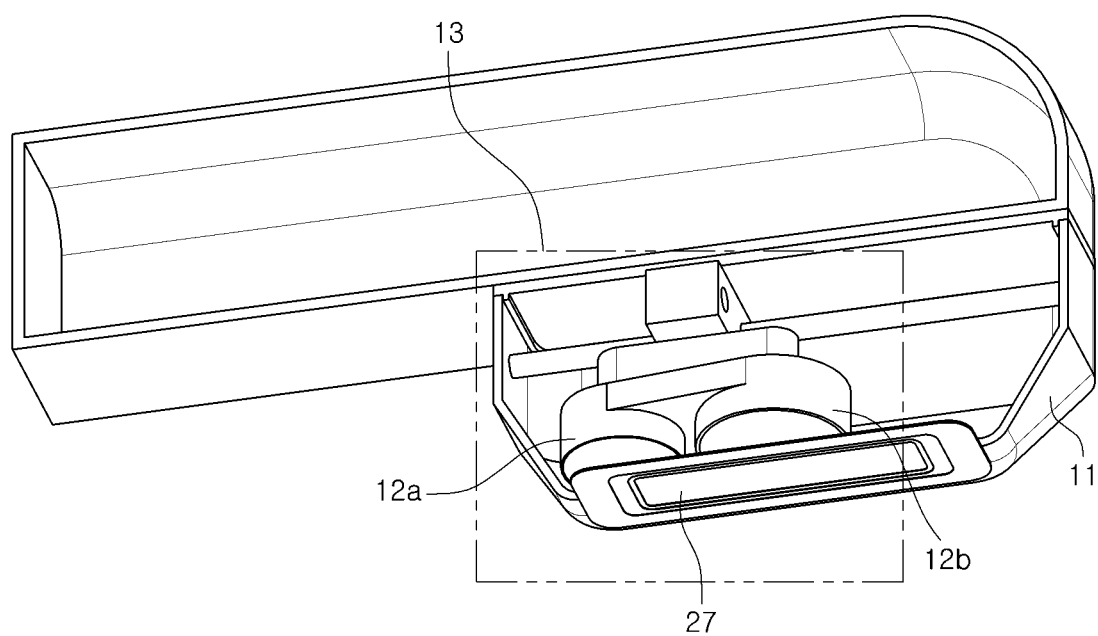
FIG. 9A is a view illustrating a state in which a film is coupled to a lower surface of the cartridge including the plurality of transducers according to an exemplary embodiment of the present disclosure.

FIG. 9A is a view illustrating a state in which a film is coupled to the lower surface of the cartridge including the plurality of transducers according to an exemplary embodiment of the present disclosure.

Figure 9B:
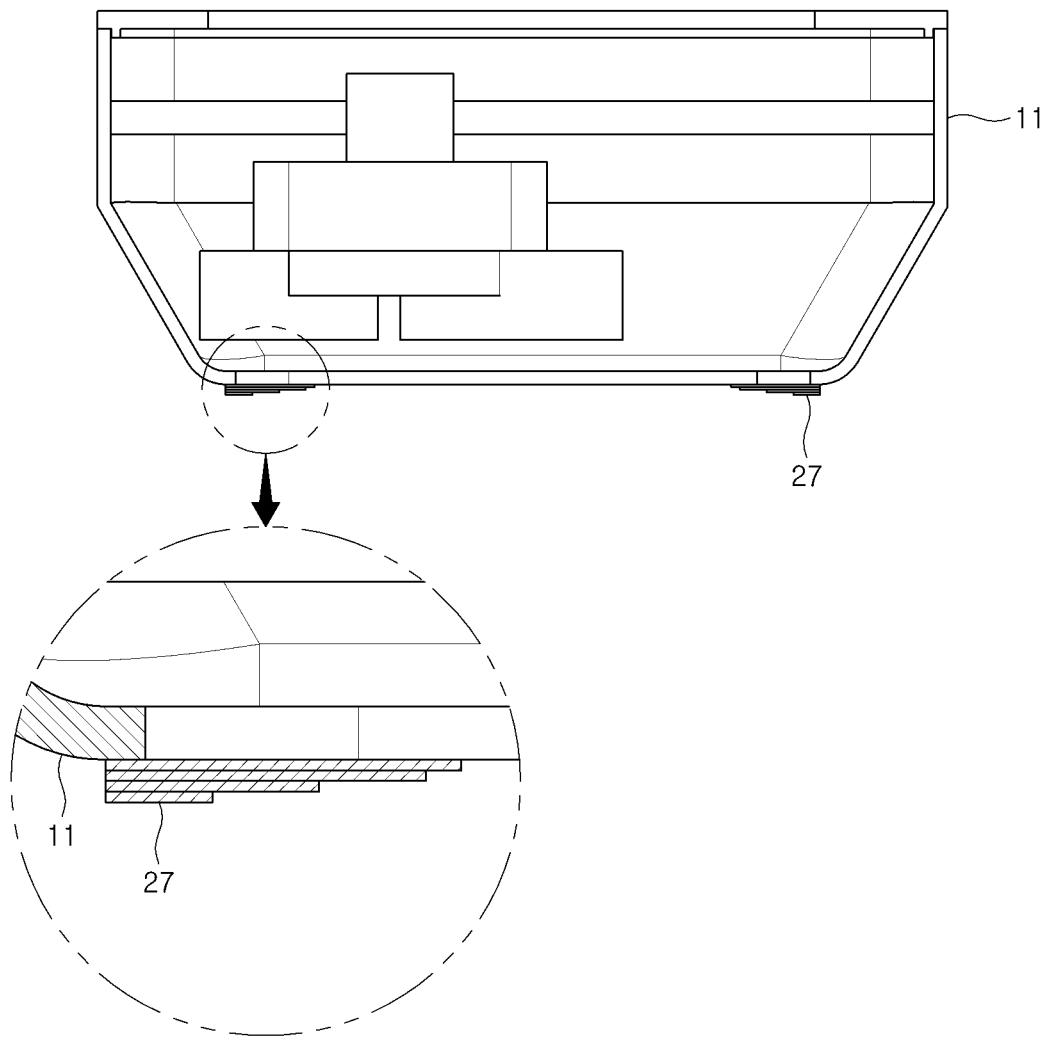
FIG. 9B is a cross-sectional view illustrating a state in which a film is coupled to the lower surface of the cartridge including the plurality of transducers according to an exemplary embodiment of the present disclosure.

FIG. 9B is a cross-sectional view illustrating a state in which a film is coupled to the lower surface of the cartridge including the plurality of transducers according to an exemplary embodiment of the present disclosure.

Figure 9C:
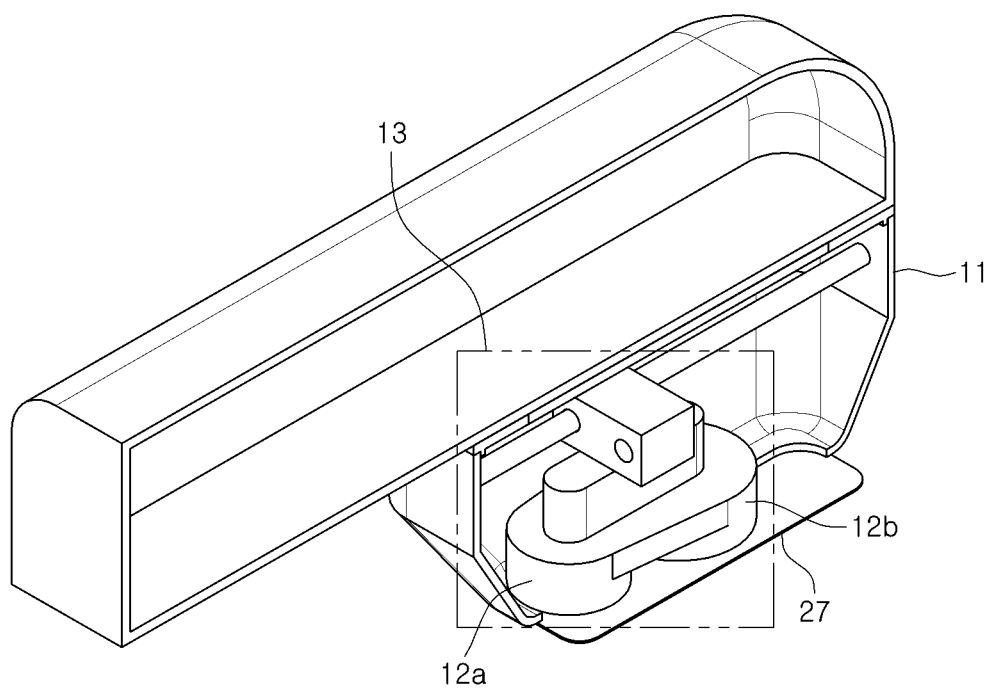
FIG. 9C is a view illustrating the cartridge in a state in which a film is coupled to the lower surface of the cartridge including the plurality of transducers according to an exemplary embodiment of the present disclosure.

FIG. 9C is a view illustrating the cartridge in a state in which a film is coupled to the lower surface of the cartridge including the plurality of transducers according to an exemplary embodiment of the present disclosure.

Referring to FIGS. 9A to 9C, the ultrasound output device including the plurality of transducers according to the present disclosure may further include a film 27.

First, referring to FIGS. 9A and 9C, the ultrasound output device of the present disclosure may further include the film 27 on the lower surface of the cartridge in order to reduce edge noise that occurs during an ultrasound procedure. The film 27 may be formed of polyimide but is not limited thereto as long as it is a transparent or non-transparent film capable of transmitting ultrasound to the surface of a biological tissue.

Referring to FIG. 9B, the film 27 may be composed of a plurality of layers and is located on the lower surface of the cartridge 11. The film 27 may be laminated to be thicker laterally from a side portion of an output unit from which ultrasound is output, so that edge noise of the output ultrasound can be reduced or ultrasonic energy can be further focused.

Figure 10:
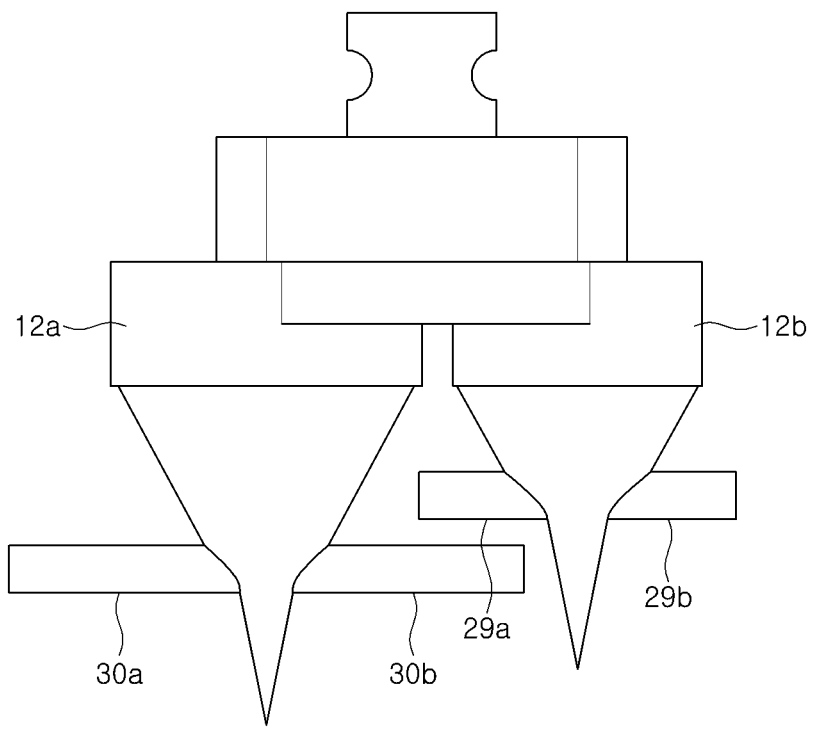
FIG. 10 is a view illustrating a state in which apertures are coupled to the plurality of transducers according to an exemplary embodiment of the present disclosure, so that focal points are adjusted.

FIG. 10 is a view illustrating a state in which apertures are coupled to the plurality of transducers according to an exemplary embodiment of the present disclosure, so that focal points are adjusted.

Referring to FIG. 10, the cartridge 11 of the ultrasound output device according to the present disclosure may further include apertures 29a, 29b, 30a, and 30b.

The apertures 30a and 30b may be positioned below the first transducer 12a to adjust a size of focused ultrasound of the first transducer 12a, and the apertures 29a and 29b may be positioned below the second transducer 12b to adjust a size of focused ultrasound of the second transducer 12b.

A material for the apertures 30a and 30b positioned on a lower surface of the first transducer 12a and the apertures 29a and 29b positioned on a lower surface of the second transducer 12b is not limited, as long as it can control the size of the focused ultrasound.

Since the size of the ultrasound focused by the apertures 30a and 30b positioned on the lower surface of the first transducer 12a and the size of the ultrasound focused by the apertures 29a and 29b positioned on the lower surface of the second transducer 12b can be adjusted, it is possible to improve, enlarge, reduce or change the size of emitted ultrasound. Accordingly, it is possible to focus suitable ultrasound according to a size or depth of lesion during a procedure.

Although the exemplary embodiments of the present disclosure have been described in detail with reference to the accompanying drawings, the present disclosure is not limited thereto and may be embodied in many different forms without departing from the technical concept of the present disclosure. Therefore, the exemplary embodiments of the present disclosure are provided for illustrative purposes only but not intended to limit the technical concept of the present disclosure. The scope of the technical concept of the present disclosure is not limited thereto. Therefore, it should be understood that the above-described exemplary embodiments are illustrative in all aspects and do not limit the present disclosure. The protective scope of the present disclosure should be construed based on the following claims, and all the technical concepts in the equivalent scope thereof should be construed as falling within the scope of the present disclosure.

What is claimed is:

1. An ultrasound output device comprising:
   a handpiece configured to be in contact with or adjacent to a surface of a biological tissue;
   a cartridge detachably coupled to a lower surface of the handpiece; and
   a transducer module embedded in the cartridge, the transducer module including a plurality of transducers arranged side by side in the cartridge,
   wherein the plurality of transducers includes a first transducer configured to transmit ultrasound to a first tissue depth and a second transducer configured to transmit ultrasound to a second tissue depth different from the first tissue depth, and
   wherein the second transducer is disposed separately from and adjacent to the first transducer, the first and second transducers respectively positioned along a line extending parallel to a lateral side of the cartridge.

2. The ultrasound output device of claim 1, further comprising:
   a housing for holding the first transducer and the second transducer; and
   a movement mechanism including a rail unit disposed in parallel with a longitudinal direction of the handpiece, a rail guide slidably coupled to the rail unit, and a junction unit for coupling the rail guide to the housing,
   wherein the movement mechanism is configured to move the plurality of transducers such that the first transducer and the second transducer are repositioned to be disposed on a line that is perpendicular to the lateral side of the cartridge.

3. The ultrasound output device of claim 1,
   wherein the first transducer transmits a frequency in a range of 0.1 MHz to 10 MHz, and
   wherein the second transducer transmits a frequency in a range of 10 MHz to 100 MHz.

4. The ultrasound output device of claim 1, wherein each of the plurality of transducers is configured to have a linear shape.

5. The ultrasound output device of claim 4, wherein each of the plurality of transducers is composed of a plurality of pieces.

6. The ultrasound output device of claim 4, further comprising:
   a shielding unit disposed on a lower surface of each of the plurality of transducers,
   wherein the shielding unit has an upper side conforming to the lower surface of a corresponding transducer of the plurality of transducers and a lower side having a shape configured to reduce edge noise in the corresponding transducer.

7. The ultrasound output device of claim 6, wherein the shielding unit has a thickness increasing from a central portion of the corresponding transducer to a side portion thereof.

8. The ultrasound output device of claim 1, wherein the cartridge includes
   an output unit from which ultrasound is output, and
   a film formed of polyimide and disposed on a lower surface of the output unit to reduce edge noise.

9. The ultrasound output device of claim 8,
   wherein the film is laminated and includes a plurality of layers formed successively on the lower surface of the output unit, and
   wherein the plurality of layers increases in number toward a side portion of the output unit such that the film is thicker toward the side portion of the output unit.

10. The ultrasound output device of claim 1,
    wherein the cartridge includes a cooling passage that encircles a bottom surface of the cartridge and includes an inlet arranged on one lateral side of the cartridge and at least one outlet arranged on the bottom surface of the cartridge, and
    wherein the cooling passage is configured to lower a temperature of the surface of the biological tissue by injecting cooling gas or cooling water into the inlet and flowing the cooling gas or cooling water to a bottom surface of the cartridge which is detachable through the at least one outlet.

11. The ultrasound output device of claim 10, wherein the inlet of the cooling passage has one end disposed at an upper side of the cartridge and configured to inject the cooling gas or cooling water, and
    wherein the at least one outlet of the cooling passage includes a plurality of outlets disposed at intervals around the bottom surface of the cartridge, the plurality of outlets formed in an inner side of the cooling passage and configured to flow the cooling gas or cooling water to the surface of the biological tissue.

12. The ultrasound output device of claim 1, further comprising:
    a driving unit allowing for a swing movement movement, the driving unit configured to rotate the plurality of transducers of the transducer module to adjust an ultrasound focus position.

13. The ultrasound output device of claim 1, further comprising:
    a movement mechanism for transmitting ultrasound to the different tissue depths.

14. The ultrasound output device of claim 13,
    wherein the movement mechanism for transmitting ultrasound to different tissue depths moves the transducer module in a vertical direction or a horizontal direction,
    wherein each of the plurality of transducers transmits ultrasound to different tissue depths according to the movement mechanism.

15. The ultrasound output device of claim 1, wherein the ultrasound transmitted from each of the plurality of transducers is a continuous wave.

16. The ultrasound output device of claim 1, further comprising:
    an aperture formed on a lower surface of each of the plurality of transducers,
    wherein a size of focused ultrasound is respectively adjusted using the aperture of a corresponding transducer of the plurality of transducers.

* * * * *